United States Patent [19]

Bible et al.

[11] Patent Number: 5,226,431
[45] Date of Patent: Jul. 13, 1993

[54] OPTICAL/ELECTRICAL TRANSCEIVER

[75] Inventors: Christopher T. Bible, Reno, Nev.; George H. Middle, Canyon Lake, Calif.

[73] Assignee: Caliber Medical Corporation, Reno, Nev.

[21] Appl. No.: 717,976

[22] Filed: Jun. 20, 1991

[51] Int. Cl.$^5$ ............................................. A61B 5/04
[52] U.S. Cl. .................................... 128/904; 128/710; 128/696
[58] Field of Search ............. 128/908, 904, 696, 710, 128/419 PT, 903, 901

[56] References Cited

U.S. PATENT DOCUMENTS

| | | | |
|---|---|---|---|
| 3,488,586 | 1/1970 | Watrous et al. | 128/908 |
| 3,742,947 | 7/1973 | Hashem | 128/696 |
| 3,794,841 | 2/1974 | Cosentino et al. | 128/908 |
| 3,882,277 | 5/1975 | DePedro et al. | 128/904 |
| 3,910,257 | 10/1975 | Fletcher et al. | 128/908 |
| 3,986,498 | 10/1976 | Lewis | 128/696 |
| 4,004,577 | 1/1977 | Sarnoff | 128/20.6 R |
| 4,173,971 | 11/1979 | Karz | 128/702 |
| 4,216,462 | 8/1980 | McGrath et al. | 128/710 |
| 4,428,381 | 1/1984 | Hepp | 128/904 |
| 4,531,527 | 7/1985 | Reinhold, Jr. et al. | 128/696 |
| 4,794,532 | 12/1988 | Leckband et al. | 128/710 |
| 4,804,950 | 2/1989 | Moon et al. | 128/710 |
| 4,883,064 | 11/1989 | Olson et al. | 128/696 |
| 4,924,875 | 5/1990 | Chamoun | 128/908 |
| 5,038,800 | 8/1991 | Oba | 128/904 |

FOREIGN PATENT DOCUMENTS 2003276A 8/1978 United Kingdom.
2130776A 8/1983 United Kingdom.

Primary Examiner—Kyle L. Howell
Assistant Examiner—Kennedy J. Schaetzle
Attorney, Agent, or Firm—Nydegger & Associates

[57] ABSTRACT

A patient monitoring system is provided which includes a monitor and a transmitter which can optically communicate with each other. The monitor receives analog physiological data from a patient and converts the analog data to a digital optical signal which is sent to the transmitter optically. The transmitter includes a memory for storing the digital signal thereby allowing separation of the monitor from the transmitter prior to subsequent transmission. Additionally, the transmitter is capable of converting the digital signal to a modulated tone for transmission via standard phone lines. In this manner, the transmitter is able to send the converted signal to a central processing system via phone lines. This converted signal can then be monitored at the central processing system or it can be further communicated to one or more remote receiving stations.

10 Claims, 2 Drawing Sheets

OPTICAL/ELECTRICAL TRANSCEIVER

FIELD OF THE INVENTION

The present invention pertains generally to medical diagnostic systems. More particularly, the present invention pertains to electrical systems which collect and monitor physiological data and then transfer this data to a remote site for medical evaluation. The present invention is particularly, but not exclusively, useful for periodically collecting physiological data from an ambulatory patient via commercially installed telephone equipment while electrically isolating the patient from this equipment.

BACKGROUND OF THE INVENTION

It is well known that various galvanometric devices can be used to detect and record the minute differences in potential between different parts of the body caused by muscle action. Perhaps the most well known such device is the electrocardiograph which measures these differences for the heart muscle. In any event, and regardless of the particular muscle action being measured, it is frequently necessary or desirable to monitor the muscle's activity over an extended period of time. This is particularly so where the heart muscle is involved.

For the particular case involving the heart muscle, it is known that some heart anomalies can be identified early and properly diagnosed by studying a history of the patient's electrocardiogram (ECG). Further, it is known that some heart anomalies can even be effectively predicted by observing trends which are disclosed in the ECG history. In order to observe these trends, however, it is necessary that the heart be continuously monitored. This, of course, requires that the patient remain "hooked up" to an electrocardiograph for an extended period of time. Additionally, in order to be useful and effective, it is necessary that the ECG history be periodically reviewed by a physician. Consequently, the problem is essentially twofold. First, there is the need to detect and record the ECG history. Second, there is the need to safely, effectively and reliably transmit this ECG history to the proper medical authorities.

Fortunately, much of the world is serviced by a vast and extensive telecommunications network which is commercially available for the transmission of data and information between remote locations. Indeed, this existing network is accessible by various types of devices, to include telephones, facsimile machines, and central processing units. The present invention recognizes that the flexibility, reliability and conveniences of this network can, and should, be effectively used for the transmission of physiological data, such as an ECG history, from a patient to proper medical personnel. Where, however, it is necessary that the device remain connected to the patient while collecting this data (e.g. an electrocardiograph compiling an ECG history) it is essential that the patient be electrically isolated from the telecommunications network.

Accordingly, it is an object of the present invention to provide a device for relaying physiological data along a communications path from a patient to an electronic data processing system which electrically isolates the patient from the telecommunications network used by the electronic data processing system. Another object of the present invention is to provide a device for establishing a communications link between a patient and a data processing system which permits the relatively rapid unloading and transmission of data from the patient into the system. Yet another object of the present invention is to provide a device for transmitting collected physiological data which is safe to use with a commercial telecommunications network. Still another object of the present invention is to provide a device for collecting and transmitting physiological data from a patient which has minimal power requirements. Another object of the present invention is to provide a device for relaying physiological data along a communications path from a patient to an electronic data processing system which is easy to use, relatively simple to manufacture and comparatively cost effective.

SUMMARY OF THE INVENTION

A device for establishing a communications link between a patient and a data processing system includes a monitor and a transmitter which can be optically coupled together for the direct transmission of physiological data from the patient into the system. The monitor itself is electrically connected to the patient and has an infrared light emitting diode (LED) which, in combination with an analog to digital (A/D) converter, changes electrical signals from the patient into an optical signal. Specifically, any electrical signal representative of physiological data which can be formatted for standard serial communications, such as an ECG, can be converted at the monitor into an optical signal. This optical signal is then sent to the transmitter which includes a photodiode that reconverts the optical signal into a reconstituted electrical signal. It is this reconstituted electrical signal which is subsequently transmitted via telephone lines to the data processing system. Additionally, the transmitter includes a microprocessor unit which first verifies receipt of a properly formatted signal from the monitor, and then prompts the monitor to retransmit in the event an improper signal is received. The transmitter also includes a memory capacity for temporary storage of data which can not be immediately transmitted, for whatever reason, into the commercial telecommunications network used by the data processing system.

In accordance with the present invention, the data processing system includes a central processing unit (CPU) which is connectable with at least one of a plurality of transmitters via appropriate telephone lines. The CPU itself is connectable with a plurality of receiving stations and can direct incoming signals from a particular transmitter to a selected receiving station. Accordingly, physiological data from a particular patient can be transmitted via telephone lines directly from the transmitter and through the CPU to the selected receiving station.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
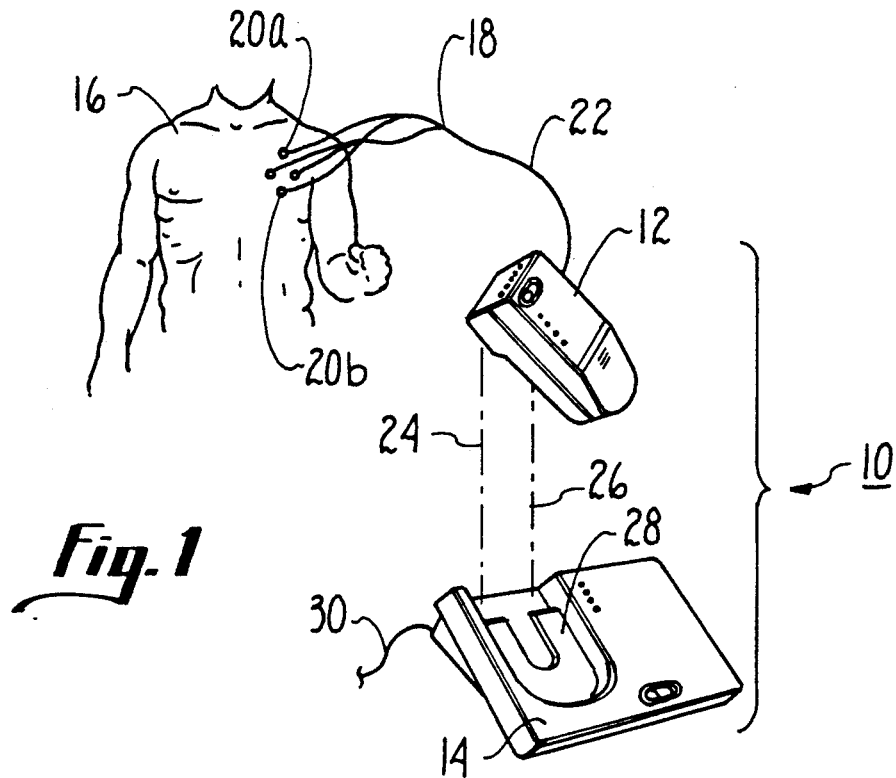
FIG. 1 is a perspective view of the apparatus of the present invention shown in its operative environment connecting a patient with a transmission line for the transfer of physiological data from a patient to a data processing system.

Referring initially to FIG. 1, the apparatus for relaying physiological data along a communications path from a patient to an electronic data processing system is shown and generally designated 10. As shown, the apparatus 10 includes a monitor 12 which can be optically coupled to a transmitter 14. At this point it is to be understood that, for purposes of the present invention, the term "optical" refers to any light wave or similar electromagnetic wave regardless whether the wave is visible or invisible.

As intended for the present invention, the monitor 12 is connected to a patient 16 through a harness 18. Specifically, the harness 18 includes a plurality of electrodes 20, such as the electrodes 20a and 20b, which are connectable on the body surface of the patient 16 for the purpose of detecting the minute differences in potential between different parts of the body caused by muscle action. In the particular case, as here, where the muscle being monitored is the heart, the harness 18 and electrodes 20 can be of types well known in the pertinent art which are useful for generating an electrocardiogram (ECG). As shown in FIG. 1, the harness 18 is electrically connected to the monitor 12 via a line 22. Thus, the minute electrical signals which are generated by contractions of the heart muscle of patient 16 are detected by the electrodes 20 and are transferred via the harness 18, and through the line 20, to monitor 12.

The operative connection between the monitor 12 and the transmitter 14 is accomplished optically. More specifically, a light path 24 and a light path 26 are established between the monitor 12 and the transmitter 14 when these components are properly positioned relative to each other. As can be appreciated with reference to FIG. 1, the light paths 24 and 26 will be substantially shortened when the monitor 12 is set into the cradle 28 of transmitter 14. Indeed, in the operation of apparatus 10, it is contemplated that the monitor 12 will be placed into the cradle 28. With this cooperation of structure, information stored in the monitor 12 can be optically transferred to the transmitter 14 for subsequent transmission as an electrical signal over a telephone transmission line 30. Importantly, this optical connection between the monitor 12 and the transmitter 14 electrically isolates the patient 16 from any electrical environment which might be connected with the transmission line 30.

Figure 2:
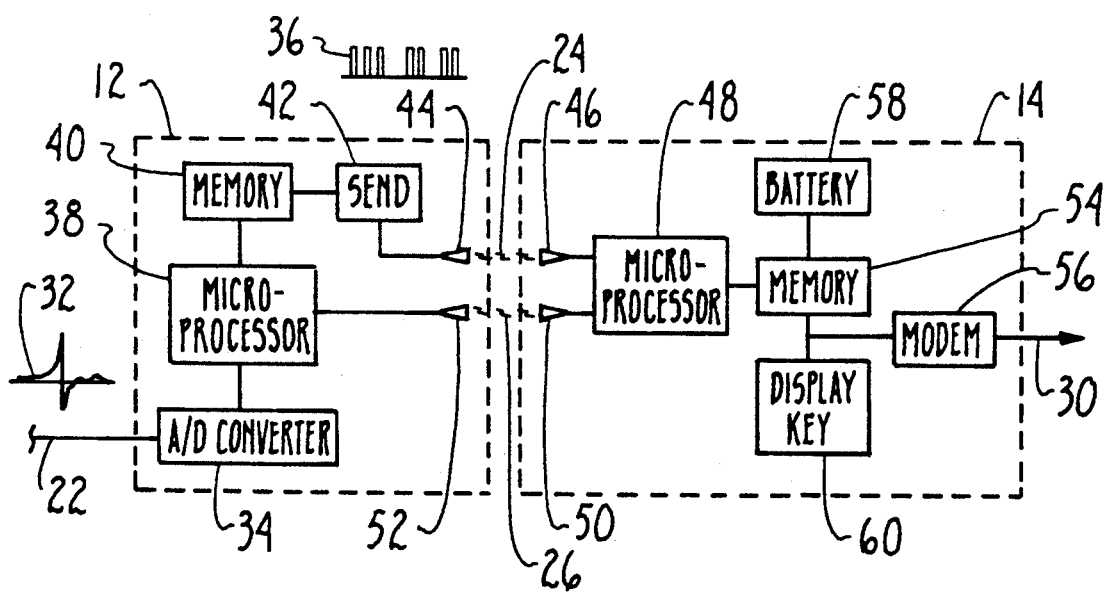
FIG. 2 is a block diagram of the interaction and cooperation of the operative components of the present invention.

The actual componentry of the apparatus 10 can, perhaps, be best appreciated by reference to FIG. 2 wherein it will be seen that monitor 12 receives an electrical signal, such as the analog signal 32, from the patient 16 over transmission line 22. An analog to digital (A/D) converter 34 receives this analog signal 32 and, in a manner well known in the art, converts it into a digital signal 36. This digital signal 36 is then received by a microprocessor 38 located in the monitor 12 where it is compared with other signals 36 which were previously received from the patient 16. By doing this comparison, the microprocessor 38 is able to determine whether any trends or substantial change may be occurring in the signals 36. If certain anomalies or questionable trends are detected, based upon comparisons made by the microprocessor 38 with certain predetermined criteria, the signal 36 is then passed to an electronic memory 40 where it is stored until the monitor 12 is operatively engaged with transmitter 14. Once the monitor 12 is properly engaged with the transmitter 14, a send unit 42 is activated and the electrical digital signal 36 is converted into an optical digital signal 36 by the interaction of the send unit 42 with a light emitting diode 44. Preferably, the light emitting diode 44 is an infrared light emitting diode of a type well known in the pertinent art. In any event, the digital signal 36 is converted at the LED 44 from an electrical signal into an optical signal.

Signal 36 is transmitted from LED 44 via light path 24 to a photodiode 46 which is mounted on the transmitter 14. Photodiode 46 is of a type well known in the pertinent art and the photodiode 46 reconverts signal 36 from an optical signal into an electrical signal. This electrically reconstructed digital signal 36 is then passed to the microprocessor 48, which is also mounted in the transmitter 14. This reconstructed signal 36, in the form in which it is received by the photodiode 46, is analyzed by the microprocessor 48 to determine whether it is properly formatted and, thus, whether it is a useable signal. If this reconstructed electrical signal 36 is not properly formatted, the microprocessor 48 causes transmitter 14 to prompt the monitor 12 to resend the signal 36. This prompting is initiated by the microprocessor 48 which electrically activates a light emitting diode in transmitter 14. The optical signal which is generated by LED 50 in response to activation from microprocessor 48 is sent along the light path 26 and is received by a photodiode 52 which is mounted on the monitor 12. The signal is then electrically transferred from the photodiode 52 to the microprocessor 38, and the microprocessor 38 is thereby prompted to resend the signal 36. This process may be repeated as necessary.

The light path 26 can, in fact, be useful for sending any useful signals from the transmitter 14 to the monitor 12. For example, When the monitor 12 is positioned in the cradle 28 of transmitter 14, preprogrammed communications can be sent along light path 26 between the microprocessor 48 of transmitter 14 and the microprocessor 38 of the monitor 12 to verify this relationship. Indeed, other useful communications can also be sent between transmitter 14 and monitor 12 in this manner depending on the needs and desires of the operator.

In addition to microprocessor 48 and the optical connection with monitor 12 made possible by photodiode 46 and LED 50, the transmitter 14 also includes a memory unit 54. Specifically, memory 54 is electrically connected to the microprocessor 48 and needs to have an information capacity which is sufficient for receipt of a complete reconstituted signal 36. Stated differently, the information capacity of memory 54 must be compatible with the sending capacity of monitor 12. Further, the memory 54 is electrically connected to a modem 56 which is able to convert the digital bits of the reconstructed signal 36 into analogue electrical impulses which can be transmitted as a modulated tone over the telephone transmission line 30. More specifically, modem 56 converts signal 36 into a telephonically transmissible signal which is representative of the physiological date contained in the signal 32. FIG. 2 also shows that the transmitter 14 includes a backup battery 58 which is connected to memory 54 in order to provide auxiliary power and preserve the information held in memory 54 in the event there is a power failure form an external power source (not shown). Also, FIG. 2 shows that the transmitter 14 has a display/key panel 60 which is electrically connected with other electrical components of transmitter 14 to indicate and control the particular mode in which the transmitter 14 is operating. For example, keys (not shown) on display/key panel 60 can be used to initiate communications from the monitor 12 and through the transmitter 14 and onto telephone transmission line 30. Further, display/key panel 60 can indicate when the transmitter 14 is transmitting and when this transmission is completed.

Figure 3:
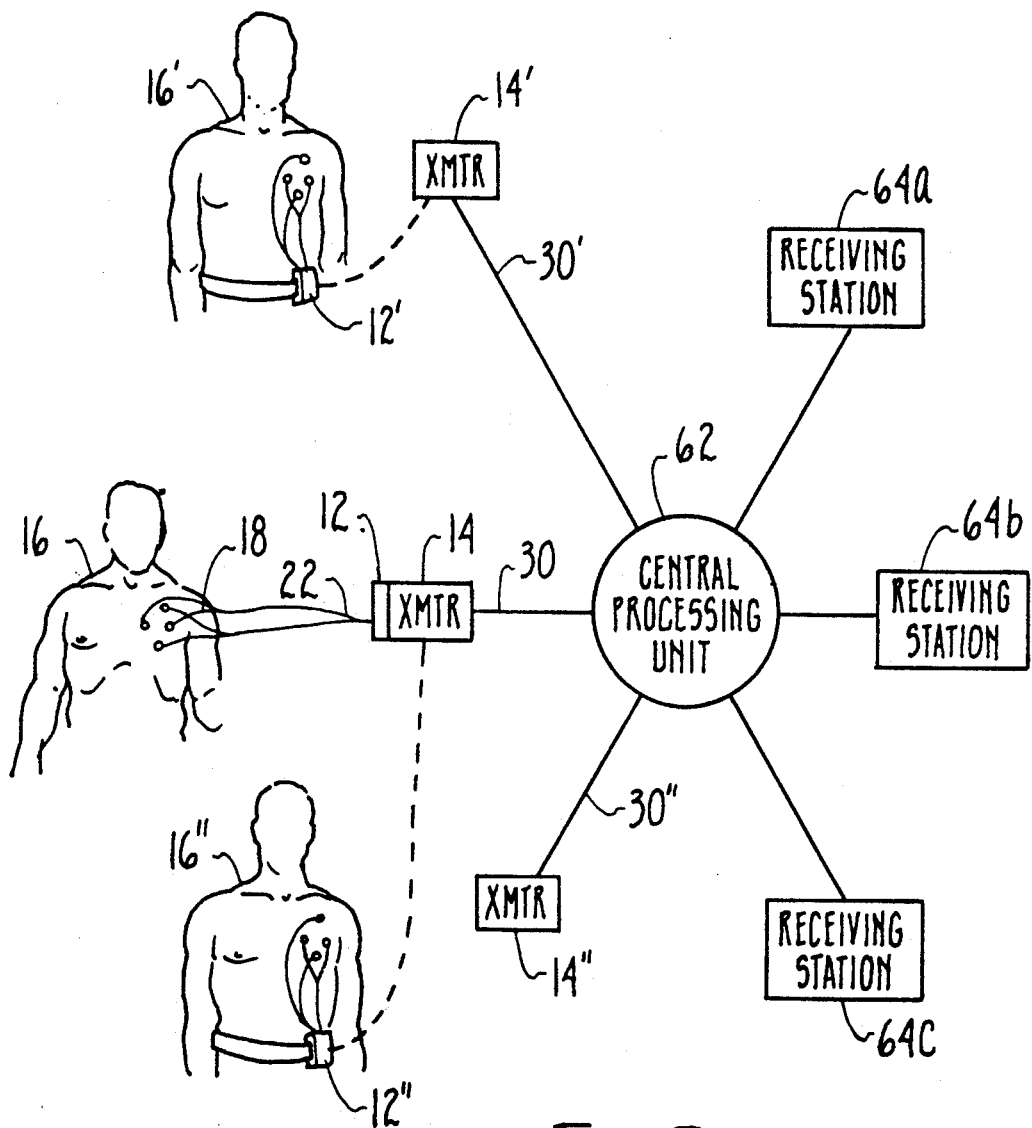
FIG. 3 is a schematic diagram showing the present invention as an interfacing component in a data processing system.

The operation of the apparatus 10 will, perhaps, be best appreciated with reference to FIG. 3. There it will be seen that individual patients (e.g. patients 16, 16' and 16") are each equipped With a respective monitor 12, 12' and 12" which is appropriately attached to the patient 16 to detect and store respective signals 32. As also shown, a plurality of transmitters 14, 14' and 14" are available for use by any one of the patients 16. Thus, for purposes of the present invention, any one of the patients 16 can connect his/her monitor 12 with any of the transmitters 14. As a practical matter, however, each patient 16 will most likely have their own transmitter 14 available for their personal use.

In accordance with the present invention, the transmitters 14 provide an interface with a data processing system which relies on a commercially available telecommunications network for the transmission of data between remote stations. Specifically, each transmitter 14, 14' and 14" is connectable through a modem 56 and a respective telephone transmission line 30, 30' and 30" to a central processing unit (CPU) 62. Consequently, the CPU 62 is able to route transmissions from any particular transmitter 14 to a selected receiving station 64a, 64b or 64c.

Thus, with the apparatus 10 and the data processing system to which it is connectable, a signal 32 which represents physiological data from a patient 16 can be communicated along a communications path directly to a selected receiving station 64 where the data can be properly evaluated by medical authorities. Importantly, the apparatus 10 electrically isolates the patient 16 from the telecommunications network of the data processing system. Consequently, the signal 32/signal 36 can be transmitted from a patient 16 to a receiving station through the apparatus 10 an additional consideration, this allows the transmission of real-time data from the patient into the data processing system.

While the particular device and apparatus for relaying physiological data along a communications path from a patient to an electronic data processing system as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. An apparatus for establishing a communications link between a patient and a data system which comprises:
   means connectable to said patient for receiving an electrical signal from said patient and converting said electrical signal into a digital optical signal;
   means for sending said digital optical signal;
   means for positionable relative to said sending means for receiving said digital optical signal and reconverting said digital optical signal into a reconstituted digital electrical signal;
   means for detecting errors in said digital optical signal sent by said sending means; and
   means connected to said receiving and reconverting means for transmitting said reconstituted digital electrical signal to said data system, said means for transmitting further comprising memory means for storing said reconstituted digital signal so as to allow transmission of said reconstituted digital electrical signal after said sending means and said receiving means are separated.

2. An apparatus for establishing a communications link between a patient and a data system as recited in claim 11 wherein said sending means includes a light emitting diode and said receiving means is a photodiode.

3. An apparatus for establishing a communications link between a patient and a data system as recited in claim 11 further comprising:
   a monitor, said monitor including said sending means;
   a transmitter, said transmitter including said receiving and reconverting means;
   a central processing unit (CPU), said CPU being connected in electronic communications with said transmitter; and
   a plurality of receiving stations, each said receiving station being connected in electronic communications with said CPU.

4. An apparatus for establishing a communications link between a patient and a data system as recited in claim 3 wherein said CPU is connected to each of said receiving stations via a telephone line and each said receiving station includes a facsimile machine.

5. An apparatus for establishing a communications link, between a patient and a data system as recited in claim 4 wherein said CPU is connected to said transmitter via a telephone line.

6. An apparatus or establishing a communications link between a patient and a data system as recited in claim 5 wherein said transmitter includes means for transmitting a second optical signal to said monitor, and said monitor includes means for receiving said second optical signal from said transmitter.

7. A remote patient monitoring system for use with a phone line, said monitoring system comprising:
   a monitor capable of receiving analog physiological data from a patient;
   means included in said monitor for converting said analog physiological data into an optical serial digital data stream;
   a transmitter with optical receiver means connectable with said monitor for receiving said optical serial digital data stream, said transmitter being separable from said monitor and connectable to said phone line;
   means included in said transmitter for converting said optical serial digital data stream to analog electrical impulses transmittable as a modulated tone over said phone line;
   means included in said transmitter for transmitting said modulated tone over said phone line;
   means included in said transmitter for storing said optical serial digital data stream allowing separation of said monitor from said transmitter prior to transmission of said modulated tone over said phone line; and a remote electronic data processing system capable of receiving said modulated tone from said phone line.

8. The system as recited in claim 7 further comprising means included in said transmitter for detecting and correcting errors in said optical serial digital data stream.

9. The system as recited in claim 7 wherein said means for converting said analog physiological data comprises an analog to digital optical converter.

10. The system as recited in claim 7 wherein said means for converting said optical serial digital data stream receives said optical serial data stream from said means for storing.

* * * * *

UNITED STATES PATENT AND TRADEMARK OFFICE
CERTIFICATE OF CORRECTION

PATENT NO. : 5,226,431

DATED : July 13, 1993

INVENTOR(S) : Chris Bible et al.

It is certified that error appears in the above-identified patent and that said Letters Patent is hereby corrected as shown below:

Col. 6, claim 2, line 3, after the word "claim" and before the word "wherein" delete the numeral "11" and insert therefor the numeral --1--.

Col. 6, claim 3, line 3, after the word "claim" and before the word "further" delete the numeral "11" and insert therefor the numeral --1--.

Signed and Sealed this

Nineteenth Day of September, 1995

Attest:

BRUCE LEHMAN

Attesting Officer     Commissioner of Patents and Trademarks